(12) United States Patent
Riss

(10) Patent No.: US 8,013,184 B2
(45) Date of Patent: Sep. 6, 2011

(54) MANUFACTURE PROCESS OF ORGANIC COMPOUNDS

(75) Inventor: Bernhard Riss, Huningue (FR)

(73) Assignee: Novartis AG, Basel (CH)

( * ) Notice: Subject to any disclaimer, the term of this patent is extended or adjusted under 35 U.S.C. 154(b) by 1116 days.

(21) Appl. No.: 11/720,854

(22) PCT Filed: Dec. 14, 2005

(86) PCT No.: PCT/EP2005/013452
§ 371 (c)(1),
(2), (4) Date: Jun. 5, 2007

(87) PCT Pub. No.: WO2006/063819
PCT Pub. Date: Jun. 22, 2006

(65) Prior Publication Data
US 2009/0234010 A1    Sep. 17, 2009

(30) Foreign Application Priority Data

Dec. 16, 2004   (GB) .................................. 0427600.2

(51) Int. Cl.
*C07C 229/00* (2006.01)
(52) U.S. Cl. ...................................................... 562/450
(58) Field of Classification Search .................... None
See application file for complete search history.

(56) References Cited

U.S. PATENT DOCUMENTS

| | | | | |
|---|---|---|---|---|
| 4,659,826 A | * | 4/1987 | Schwarz | 544/277 |
| 5,773,647 A | | 6/1998 | Leone-Bay et al. | 562/444 |
| 7,420,085 B2 | * | 9/2008 | Bhandarkar et al. | 562/450 |
| 2004/0242478 A1 | | 12/2004 | Azria et al. | 514/12 |

FOREIGN PATENT DOCUMENTS

| | | |
|---|---|---|
| CN | 1446795 A | 10/2003 |
| EP | 0 576 941 | 1/1994 |
| WO | WO 00/07979 * | 2/2000 |
| WO | 00/59863 | 10/2000 |
| WO | 03/015822 | 2/2003 |

OTHER PUBLICATIONS

Leone-Bay A et al., "Synthesis and Evaluation of Compounds that Facilitate the Gastrointestinal Absorption of Heparin", Journal of Medicinal Chemistry, American Chemical Society, vol. 41, No. 7, pp. 1163-1171, (1998).

* cited by examiner

*Primary Examiner* — Noble Jarrell

(74) *Attorney, Agent, or Firm* — David Kurlandsky; Leslie Fischer

(57) ABSTRACT

The present invention relates to a method of preparing N-substituted salicylamides or derivatives thereof and their derivatives, e.g. their salts. In particular, the present invention relates to a method of preparing (N-(5-chlorosalicyloyl)-8-aminocaprylic acid (5-CNAC) and its corresponding disodium monohydrate.

15 Claims, No Drawings

MANUFACTURE PROCESS OF ORGANIC COMPOUNDS

The present invention relates to a method of preparing N-substituted salicylamides or derivatives thereof and their derivatives, e.g. their salts. In particular, the present invention relates to a method of preparing (N-(5-chlorosalicyloyl)-8-aminocaprylic acid (5-CNAC) and its corresponding disodium monohydrate.

The N-substituted salicylamides as prepared by the method of the present invention are suitable for use in compositions for delivering active agents via oral or other routes of administration to mammals.

BACKGROUND TO INVENTION

Processes for preparing N-substituted salicylamides are known such as that shown in Scheme 1.

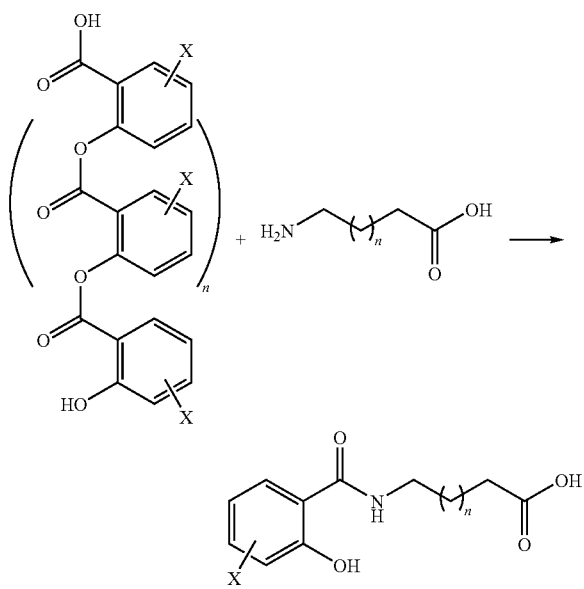

The oligosalicylate is obtained from the corresponding salicylic acid upon treatment with acetic anhydride. Coupling of the amino acid is promoted with a base, preferably potassium carbonate in a suitable solvent (like dioxane). Yields are generally in the order of 50%.

An exemplary compound synthesised by this prior art process is 5-CNAC, which is commonly used as a delivery agent for therapeutic agents and is used in pharmaceutical compositions.

SUMMARY OF THE INVENTION

The invention provides, amongst other things, a method for making N-substituted salicylamides in which a salicylic acid or a salicylic acid whose carboxy group is derivatised, for example an ester or a derivative comprising a peptide coupling agent, in any event unprotected at its phenolic hydroxy group, is reacted with an amine under basic conditions, i.e. conditions in which at least a proportion of the phenolic hydroxy group is deprotonated, in an aprotic solvent, e.g. DMF (dimethylformamide). The carboxy group of the starting salicylic acid is typically esterified or otherwise derivatised, e.g. activated.

The invention further provides a method for making a salt of an N-substituted salicylamide, where an N-substituted salicylamide is contacted with a base, e.g. an alkali metal base, for example by contacting the salicylamide with a basic aqueous solution containing an alkali metal (or other) cation. Normally the aqueous solution comprises an acetone/water mixture.

In particular, the present invention relates to a method of preparing (N-(5-chlorosalicyloyl)-8-aminocaprylic acid (5-CNAC) and its salts, notably its corresponding disodium monohydrate. The method comprises reacting methyl-5-chloro-salicylate with amino-octanoic acid (or derivative thereof, for example amino-octane-nitrile) under basic conditions in an aprotic solvent, e.g. dimethylformamide. The basic conditions may be created by pre-reacting the methyl-5-chloro-salicylate with a base such as, for example, an alcoholate, e.g. NaOMe, or by including the base in the reaction mixture. The disodium monohydrate salt may be formed by reacting the 5-CNAC with NaOH in an acetone/water mixture.

The N-substituted salicylamides, especially 5-CNAC, as prepared by the method of the present invention are suitable for use in compositions for delivering active agents via oral or other routes of administration to mammals. The method may therefore further comprise incorporating the salicylamide, whether as free acid, ester or salt, into a pharmaceutical composition containing also an active agent. The composition typically contains a pharmaceutically acceptable diluent or excipient as well as an active agent.

DETAILED DESCRIPTION OF THE PRESENT INVENTION

The present invention relates in embodiments to a method of preparing N-substituted salicylamides or derivatives thereof and their salts from the corresponding un-protected salicylic acid ester as shown in Scheme 2. The phenolic hydroxy group is unprotected. The carboxy group of the acid may be in the form of the free acid, but usually it is derivatised, e.g. esterified or activated as illustrated in Scheme 2:

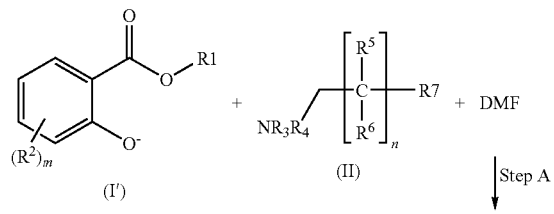

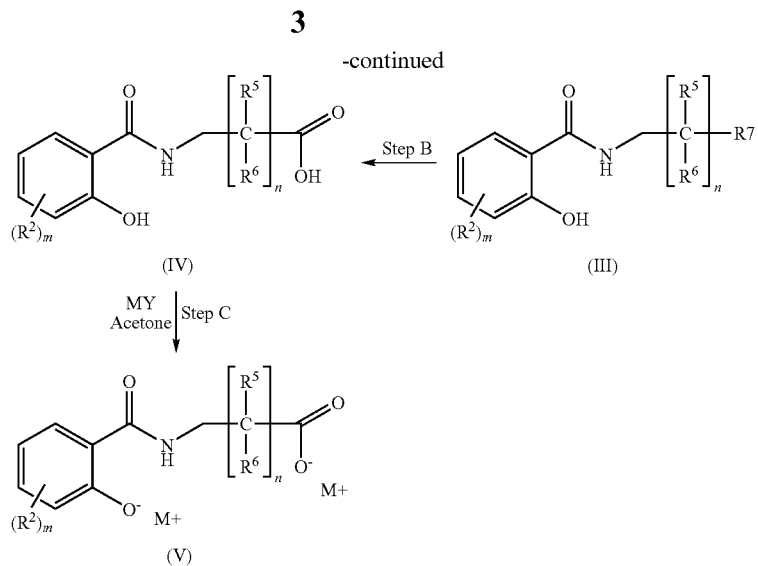

where M is an alkali metal.

The species of formula (I') may be formed by deprotonation of compounds of formula (I) below by reaction with a base. The base may be an alcoholate, for example an alkali metal alcoholate, such as, e.g. alkoxide. Species of formula (I') may be formed prior to step A, or may be formed in situ during step A by including a base in the salicylate/amino acid/DMF reaction mixture.

The source of species of formula (I') may therefore be a preformed salt, for example in the case that the base is an alkali metal alcoholate, then the compound of formula (I') may be in the form of the alkali metal salt; for example if NaOMe were used, then the compound of formula (I') may be in the form, fully or partially, of the sodium salt. In an alternative set of compounds, compounds of formula (I') may be in the form of other salts, such as an ammonium salt. The deprotonation step is exemplified in Scheme 4:

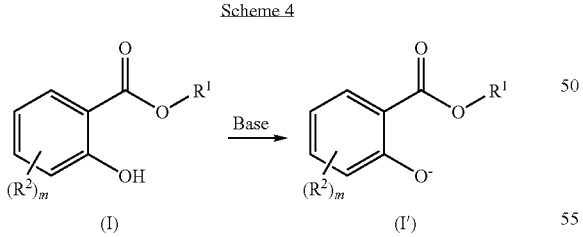

Step B may be a single step reaction, involving acid work up of a compound in which $R^7$ is a carboxyl group. In other cases, $R^7$ must be converted into a carboxyl group, for example by hydrolysis of a nitrile group; in this instance, step B comprises the conversion reaction and, if appropriate, a subsequent work up to the acid. Thus, embodiments are shown in reaction schemes B1 and B2:

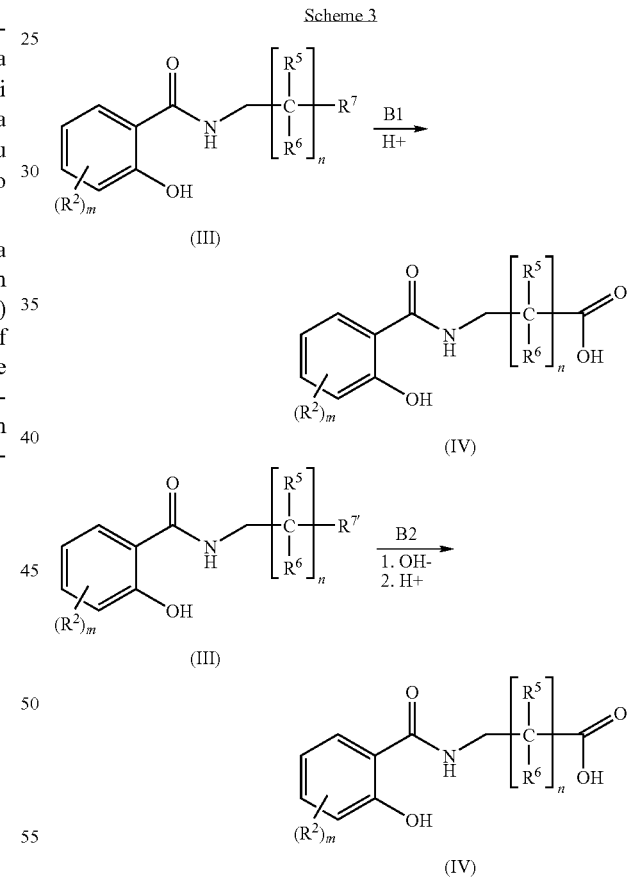

where $R^{7'}$ is not carboxy.

Scheme B1 illustrates a class of reactions where compound (III) can be converted to compound (IV) by treating it with acid, as in the case where $R^7$ comprises carboxyl groups in the form of a salt.

Scheme B2 illustrates a class of reactions where $R^7$ is converted to a carboxy group by base hydrolysis, as for example in the case of a nitrile group. After the hydrolysis is performed, the base is contacted with an acid to convert the carboxly groups into the acid form.

The reaction steps A, B and C, although shown in sequence, may be carried out independently of one another, especially step C.

In the above schemes, the symbols have the following meanings:

n is from 1 to 8, preferably n is 6;

m is from 1 to 4, preferably m is 1;

$R^1$ is an ester-forming group, e.g. a linear or branched alkyl containing 1, 2, 3, 4, 5 or 6 carbon atoms, halogen, or other carboxy activating group such as, for example, hydroxysuccinamidyl, hydroxysuccinimidyl or pentafluorophenyl or any peptide coupling reagent such as, for example, carbonyl diimidazol, dicyclihexyl carbodiimide, phosphoric anhydride; and the or each $R^2$ may be independently selected from —OH, $NR^3R^4$, halogen, $C_1$, $C_2$, $C_3$ or $C_4$ alkyl, $C_1$, $C_2$, $C_3$ or $C_4$ haloalkyl, $C_1$, $C_2$, $C_3$ or $C_4$ alkoxy, $C_1$, $C_2$, $C_3$ or $C_4$ alkenyl; and the or each $R^5$ and each $R^6$ are independently selected from hydrogen, —OH, $NR^3R^4$, halogen, $C_1$, $C_2$, $C_3$ or $C_4$ alkyl, $C_1$, $C_2$, $C_3$ or $C_4$ alkoxy, $C_1$, $C_2$, $C_3$ or $C_4$ alkenyl and each $R^5$ and each $R^6$ are not required to be the same; and $R^3$ and $R^4$ are each independently selected from hydrogen, —OH, $C_1$, $C_2$, $C_3$ or $C_4$ alkyl, $C_1$, $C_2$, $C_3$ or $C_4$ haloalkyl, $C_1$, $C_2$, $C_3$ or $C_4$ alkoxy, $C_1$, $C_2$, $C_3$ or $C_4$ alkenyl.

Halogen, a preferred $R^2$ group, may be selected from chloro, fluoro, bromo and iodo. Most preferred as $R^2$ is chloro.

In a preferred embodiment every $R^5$ and every $R^6$ is hydrogen.

Preferably $R^1$ is alkyl and comprises 1, 2, 3 or 4 carbon atoms and particularly comprises 1 or 2 carbon atoms. In an exemplary embodiment, $R^1$ is methyl.

Most preferably $NR^3R^4$ is $NH_2$.

Most preferably, m is 1 and $R^2$ is Cl. Particularly preferably $R^2$ is located at position 5.

$R^7$ is a carboxy group (—COOH) or moiety convertible to a carboxy group, for example an amide or nitrile. Preferably, $R^7$ is a protected carboxy group or equivalent, i.e. a moiety which will be substantially inert to reaction with —$NR^3R^4$ groups during step A but convertible thereafter to a carboxy group. Nitrile is preferred.

When $R^7$ is a nitrile, step B is preferably step B2. When $R^7$ is a carboxy group, Step B is preferably step B1.

M is an alkali metal and may be K or Li. Most preferably, the alkali metal M is Na (and therefore M+ is Na+). Y is a basic counterion, e.g. carbonate or hydroxide. Particularly preferably MY is NaOH.

In compounds (I), (III) and (IV), the phenolic hydroxy group may be in the form of a salt, for example a sodium salt.

Compounds of the formula (IV) or (V) may contain trace amounts of DMF. Preferably, the compounds contain less than 1% DMF e.g. less than 0.1%, such as less than 0.05% DMF. The amount of DMF present is suitably measured by headspace gas chromatography.

Compounds of the formula (V) may be hydrates, for example mono-, di-, tri-, tetra-, penta- or hexa-hydrates. In particular, compounds of formula V are monohydrates:

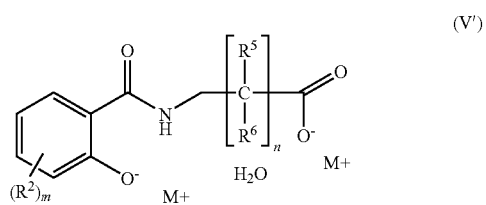

(V')

A particularly preferred compound of formula (IV) has the structure:

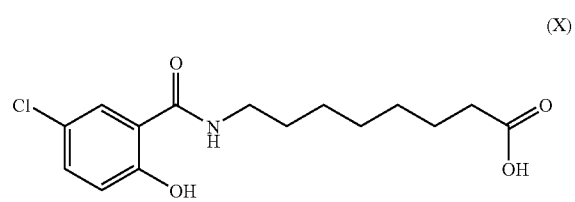

(X)

A particularly preferred compound of formula (V) is:

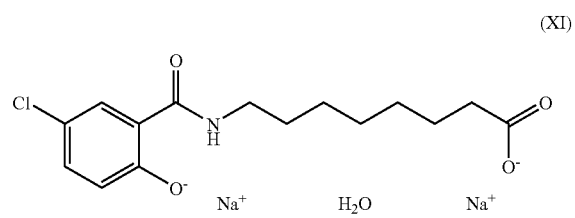

(XI)

The invention includes the preparation of anhydrides. Included also is the transformation of the acid (IV) or salt (V) to alternative solvates, alternative salts and/or to ester or other prodrug forms.

The process of the present invention may be conducted under the following exemplary conditions:

Step A

React compounds I and II under basic conditions in DMF. The basic conditions, which will cause at least a proportion of the OH groups to be O⁻, may be created by pre-reacting the compound of formula (I) with a strong base (e.g. NaOMe or another alcoholate), or by including a strong base in the reaction mixture. Typically, the reaction is carried out at an elevated temperature of, e.g., at least 90° C. and often no more than 125° C. (e.g. from 95° C. to 110° C.) and in practice the mixture is stirred. The duration of the reaction may be from, for example, about 6 to 12 hours.

Step B

B1

If the product of step A comprises a salt, it is subjected to acid work-up, for example as follows: at a temperature of, for example from about 30° C. to about 55° C. for example 40° C. to 50° C., the product is treated with acid, e.g. hydrochloric acid (25-50% m/m, e.g. 30-40% m/m). The resultant acid is isolated. If the resulting product forms a suspension, the mixture may be cooled, for example, to about 5-0° C. and the solid collected by e.g. filtration. If the resulting product is in solution (or partially in solution) the product solution may be extracted, by e.g. ethylactetate, the solvent evaporated to dryness. The product (IV) may be recrystalised in e.g. hot ethanol/water.

If $R^7$ of compound (II) is not a carboxy group, it is then, following step A, converted to a carboxy group. For example, a nitrile may be reacted with a base, e.g. NaOH. In some methods, a nitrile and NaOH or another strong base in e.g. aqueous solution are refluxed, suitably for up to 3 hours, to form the corresponding sodium carboxylate. Following the disappearance of the e.g. nitrile group, the solution may then be treated with a strong acid, for example concentrated sulphuric acid at a temperature of e.g. from about 30° C. to about 55° C., for example 40° C. to 50° C. The product is then isolated, e.g. extracted with an organic solvent for example an alkyl ester, e.g. ethylacetetate. Suitably, the solvent is then evaporated to dryness and the product (IV) recrystallised in, e.g., hot ethanol/water Step C Step C is itself inventive. Compound (IV), acetone and water are combined. The acetone:water ratio may be from about 5:1 v/v to about 15:1 v/v, e.g. about 10:1 to 11:1. A base is added to the mixture suitably at a slightly elevated temperature, e.g. about 40° C. to 60° C., for example 45° C. to 55° C. Further acetone may be added, for example as an acetone/water mixture, (e.g. from 2:1 v/v to 4:1 v/v, such as 3:1 v/v), suitably keeping the temperature at a moderately elevated level (e.g. 45° C.-55° C.). The salt is then isolated. One procedure is as follows: if the temperature is above 50° C., it is reduced to 50° C. or less (e.g 40° C. to 50° C. such as 45° C. to 48° C.) and seed crystals are added to induce crystallisation, before further reducing the temperature (e.g. to 0° C. to 5° C.) to finish the crystallisation step prior to isolating the crystals. Stirring is suitably continued throughout. The crystals may be dried under vacuum 50-60 mbar at 50-55° C. for at least 24 hours.

The processes of this invention where carried out in the presence of a strong base, may be carried out in the presence of alkali metal or alkaline earth metal hydroxides, hydrides, amides, alkanolates, phenolates, acetates, carbonates, dialkylamides or alkylsilyl-amides; alkylamines, alkylenediamines, optionally N-alkylated, optionally unsaturated, cyclo-alkylamines, basic heterocycles, ammonium hydroxides, as well as carbocyclic amines.

Alkyl-alkali metals may be selected from, for example, methyllithium, n-butyllithium, or tertbutyllithium optionally activated with tetramethylethylene diamine (TMEDA).

Alkali metal hydrides, may be selected from, for example, sodium hydride and calcium hydride.

Alkali metal amides may be selected from, for example, lithium amide or lithium diisopropylamide (LDA), lithium diethylamide, lithium isopropylcyclohexylamide or potassium bis(trimethylsilyl)amide.

Alkali metal alcoholates or alkali metal alcoholates may be selected from, for example, primary, secondary or tertiary aliphatic alcohols containing 1 to 10 carbon atoms, e.g. sodium, potassium or lithium methylate, sodium, potassium or lithium ethylate, sodium, potassium or lithium n-propylate, sodium potassium or lithium isopropylate, sodium, potassium or lithium n-butylate, sodium, potassium or lithium sec-butylate, sodium, potassium or lithium tert-butylate, sodium potassium or lithium 2-methyl-2-butylate, sodium, potassium or lithium 2-methyl-2-pentylate, sodium, potassium or lithium 3-methyl-3-pentylate, sodium potassium or lithium 3-ethyl-3-pentlyate.

Alkaline earth metal phenolates may be selected from, for example, alkaline metal O-alkyl substituted phenolates, alkali metal phenolates or alkali metal O-alkyl substituted phenolates, e.g. sodium or potassium o-cresolate.

Amine-based organic bases may be selected from, for example, 2,4,6-Trimethylpyridine; 2-tert-Butyl-1,1,3,3-tetramethyl-guanidine; 1,8-Diazabicyclo[5.4.0]undec-7-ene (DBU); 2,3,4,6,7,8,9,10-Octahydropyrimidol[1,2-a]azepine; 1,5-Diazabicyclo[4.3.0]non-5-ene (DBN); diazabicyclooctane (DABCO), 1,4-Diazabicyclo(2.2.2)octane (TED); N,N-Dicyclohexylmethylamine; N,N-Diethylaniline; N,N-Diisopropyl-2-ethylbutylamine; N,N-Diisopropylmethylamine; N,N-Diisopropyl-3-pentylamine; N,N-Dimethylaniline; 2,6-Di-tert-butyl-4-methylpyridine; N,N-Diisopropylethylamine; 2,6-Dimethylpyridine; 7-Methyl-1,5,7-triazabicyclo(4.4.0)dec-5-ene (MTBD); 3,3,6,9,9-Pentamethyl-2,10-diazabicyclo-(4.4.0)dec-1-ene (PMDBD); 1,2,2,6,6-Pentamethylpiperidine (PMP); Triethylamine; 1,1,3,3-Tetramethylguanidine (TMG); N,N,N',N'-Tetramethyl-1,8-naphthalenediamine; 2,2,6,6-Tetramethylpiperidine (TMP); 1,5,7-Triazabicyclo(4.4.0)dec-5-ene, 1,3,4,6,7,8-Hexahydro-2H-pyrimido[1,2-a]pyrimidine (TBD); Tributylamine; 2,4,6-Tri-tert-butylpyridine; Tris(trimethylsilyl)amine; and alkyl-ammonium hydroxides.

However, a mixture of the above bases may also be employed.

Those which may be mentioned by way of example are sodium hydroxide, hydride, amide, methanolate, acetate, carbonate, potassium tert.-butanolate, hydroxide, carbonate, hydride, lithium diisopropylamide, potassium bis(trimethylsilyl)-amide, calcium hydride, triethylamine, diisopropylethylamine, triethylenediamine, cyclohexylamine, N-cyclohexyl-N,N-dimethyl-amine, N,N-diethylaniline, pyridine, 4-(N,N-dimethylamino)pyridine, quinuclidine, N-methylmorpholine, benzyltrimethylammonium hydroxide, as well as 1,5-diazabicyclo[5.4.0]undec-5-ene (DBU).

In the processes of this invention the preferred bases are alkali metal alcoholates, the alkali metal preferably being sodium or potassium and the alcoholate being preferably derived from a primary alcohol. Particularly preferred strong bases are therefore e.g. sodium or potassium methylate, ethylate or n-propylate. The alkali metal alcoholates may also be prepared in situ by reacting the appropriate alcohol with the alkali metal. A particularly preferred alcoholate is sodium methylate.

The aprotic solvents suitable for use in this invention may include, but are not limited to, the following: nitrile and nitro compounds (e.g., acetonitrile, benzonitrile, nitromethane), amide and cyclic amide compounds (e.g., N,N-dimethylformamide, N-methylformamide, N,N-diethylformamide, N-ethylformamide, N,N-dimethylacetamide, N-methyl-2-pyrrolidone, hexamethylphosphoramide), ester, cyclic ester, and ether compounds (e.g., tetrahydrofuran, propylene carbonate, ethylene carbonate, gamma-butyrolactone, ethyl acetate, dimethylether), oxide and sulfo compounds (e.g., dimethylsulfoxide, acetone, sulfolane, dimethylsulfone).

Preferably, the aprotic solvent is an amide selected from N,N-dimethylformamide, N-methylformamide, N,N-diethylformamide, N-ethylformamide, N,N-dimethylacetamide. Most preferably, the solvent is N,N-dimethylformamide.

Any of the products of the process of the invention, i.e. any products of the formula III, IV or V may contain trace amounts of DMF, e.g. less than 1% DMF. Preferably, the compounds contain less than 1000 ppm DMF, e.g. less than 500 ppm DMF.

The new method is superior to the prior art with regard to its convenience and the high yield of the salicyloyl amino acid obtained (generally >90%).

A second aspect of the present invention relates to the use of the N-substituted salicylamides and derivatives thereof, in particular 5-CNAC, and their corresponding salts, in particular their disodium monohydrate salts, as prepared by the method of the present invention, for delivering active agents, such as biologically or chemically active agents, to a target.

A third aspect of the present invention relates to pharmaceutical compositions of the N-substituted salicylamides and derivatives thereof and salts thereof as prepared by the method of the present invention. In particular the present invention relates to pharmaceutical compositions comprising 5-CNAC as prepared by the method of the present invention.

A fourth aspect of the present invention relates to a pharmaceutical formulation of the N-substituted salicylamides and derivatives thereof and salts thereof as prepared by the method of the present invention. In particular the present invention relates to pharmaceutical formulations comprising 5-CNAC as prepared by the method of the present invention.

In a fifth aspect of the present invention, there is provided a method for converting an acid of formula (IV) into a base addition salt thereof, comprising combining the acid and the base in an acetone/water mixture and causing or allowing the salt to precipitate.

Included are processes which comprise converting a compound of formula (IV) or a compound of formula (V) into a pharmaceutical formulation having at least one active ingredient.

Throughout the description and claims of this specification, the words "comprise" and "contain" and variations of the words, for example "comprising" and "comprises", means "including but not limited to", and is not intended to (and does not) exclude other moieties, additives, components, integers or steps.

The disclosure hereinafter exemplified the present invention in terms of the synthesis of 5-CNAC (VI). However, it will be appreciated that the discussion of the invention in these terms is not intended to limit the scope of the invention, which is intended to extend to the N-substituted salicylamides of general formula IV. The discussion of the synthesis in terms of 5-CNAC merely represents a preferred embodiment of the present invention.

EXAMPLE 1

Preparation of N-(5-chlorosalicyloyl)-8-aminocaprylic acid from amino-octane-nitrile

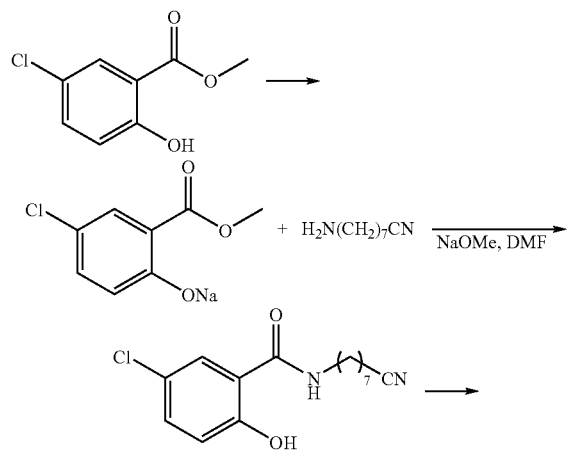

-continued

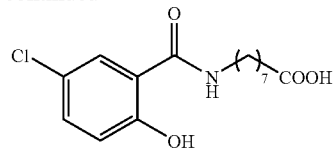

A round bottomed flask, equipped with a magnetic stirrer, is charged under nitrogen with the sodium salt of methyl-5-chloro-salicylate (20.8 g, 100 mmole), prepared from methyl-5-chloro-salicylate and sodium methylate in toluene, 8-amino-octane-nitrile (14.8 g, 105 mmole) and dimethylformamide (150 mL). The solution is heated to 100-110° C. and stirred over night. The next morning a process steering control showed less than 1.5% of starting material. The clear slightly brown solution was therefore concentrated to dryness (rotavapor) to yield a waxy solid (44.4 g). The latter was treated with sodium hydroxide (20 g in 180 ml water) and stirred under reflux over approximately three hours. Again, a process steering control showed the disappearance of the nitrile intermediate. The solution was then treated at 50° C. with about 20 g of conc. Sulphuric acid. Then ethyl acetate (150 ml) is added and the emulsion acidified with further 33 g of sulphuric acid (pH 1.7). Then, the aqueous phase is removed, and the remaining organic phase washed twice with water (50 ml each). The organic phase was then concentrated to dryness (rotavap) to yield 42 g of a solid residue, with was dissolved in hot ethanol/water (112 ml ethanol 95%, 168 ml water). At 65° C. the clear solution was saturated with 56 ml water, inducing the desired product to crystallise. The suspension was then cooled to 0° C. and stirred for an hour. Finally, the solid was collected by filtration and dried under vacuum to yield a pure compound (26.4 g, 85% of the theory).

EXAMPLE 2

Preparation of N-(5-chlorosalicyloyl)-8-aminocaprylic acid from amino-octanoic acid

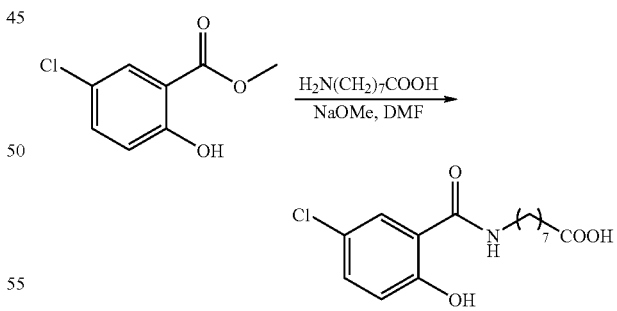

A round bottomed flask, equipped with a magnetic stirrer, is charged under nitrogen with methyl-5-chloro-salicylate (18.7 g, 100 mmole), 8-amino-octanoic acid (15.2 g, 95 mmole) and dimethylformamide (60 mL). To the suspension is added a solution of sodium methylate (35.1 g a 30% m/m). The suspension was then heated to 95-100° C., whereas methanol distilled off. After 24 h stirring, a control showed 98% conversion. Therefore, water was added (160 ml), followed at 40° C. by hydrochloric acid (22 ml, 37% m/m) to drop the pH to a value of 2.2. The suspension formed was then cooled to 0° C., and the solid collected by filtration, to yield after drying the compound (28 g, 88% of theory).

EXAMPLE 3

Preparation of the di-sodium salt, monohydrate of N-5-(chlorosalicyloyl)-8-aminocaprylic acid

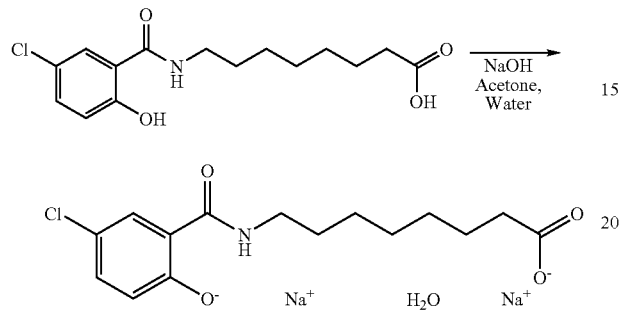

N-5-(chlorosalicyloyl)-8-aminocaprylic acid (3.5 kg, 11.15 mol), acetone (9450 ml) and water (875 ml, purified) were placed in a 50 liter vessel under a nitrogen atmosphere and stirred at 45-55° C. (jacket 60° C.) until a clear solution was formed (20 to 30 minutes). Sodium hydroxide (297 g, 30% w/w, 22.3 mol) was added in such a way as to maintain the temperature at 45-55° C., followed by a solution of acetone/water 3:1 v/v (1050 ml). The hot (50° C.) solution was passed then over a polishing filter and the filtrate transferred to an other clean vessel heated to 45 to 55° C. The transfer line was rinsed with hot (45-55° C.) acetone/water 3:1 v/v (1050 ml), and then acetone (about 10.5 liter) was added in such a way to keep the temperature around 45-55° C. (jacket 55° C.). Then, the temperature was lowered to 45-48° C. and seed crystals (4 g) were added. The mixture was stirred for about 20-30 minute to obtain a fine suspension and induce crystallization, then more acetone (28 l) were added over one hour in such a way as to maintain a temperature of 45-50° C. (jacket 55° C.). Afterwards, a slow stirring was prolonged for one hour at 45-50° C., then the temperature was lowered to 0-5° C. over a period of two hours. Stirring was continued at 0-5° C. for an hour, then crystals were collected by centrifugation, washed with cold acetone/water 95:5 v/v (7 l) and dried under vacuum 50-60 mbar at 50-55° C. for at least 24 hours to yield 4.19 kg of 5-CNAC di-sodium monohydrate (95% yield).

The invention claimed is:

1. A method for preparing a compound of formula IV:

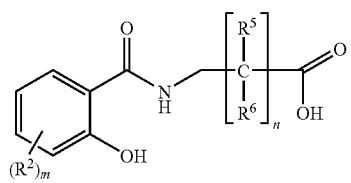

the method comprising (i) reacting a compound of formula I

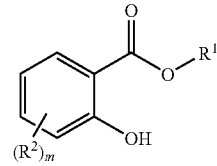

with a compound of formula II

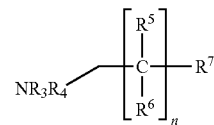

under basic conditions in which at least a portion of the phenolic hydroxy group is present in deprotonated form, in an aprotic solvent, to form a compound of formula III

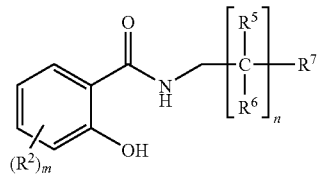

to form the compound of formula IV in the case where $R^7$ is a carboxy group, or to form a compound of formula III in the case where $R^7$ is not a carboxy group;

(ii) converting $R^7$ in the compound of formula III to a carboxy group to form the compound of formula IV;

and wherein n is from 1 to 8;

m is from 1 to 4;

$R^1$ is an alkyl group selected from methyl, ethyl, propyl, isopropyl and tert-butyl;

each $R^2$ is independently selected from —OH, $NR^3R^4$, halogen, $C_1$, $C_2$, $C_3$ or $C_4$ alkyl, $C_1$, $C_2$, $C_3$ or C4 haloalkyl, $C_1$, $C_2$, $C_3$ or $C_4$ alkoxy, $C_2$, $C_3$ or $C_4$ alkenyl;

each $R^5$ and each $R^6$ are independently selected from Hydrogen, —OH, $NR^3R^4$, halogen, $C_1$, $C_2$, $C_3$ or $C_4$ alkyl, $C_1$, $C_2$, $C_3$ or $C_4$ alkoxy, $C_2$, $C_3$ or $C_4$ alkenyl;

$R^3$ and $R^4$ are each independently selected from hydrogen, —OH, $C_1$, $C_2$, $C_3$ or $C_4$ alkyl, $C_1$, $C_2$, $C_3$ or $C_4$ haloalkyl, $C_1$, $C_2$, $C_3$ or $C_4$ alkoxy, $C_2$, $C_3$ or $C_4$ alkenyl; and $R^7$ is a carboxylic acid or amide group or nitrile group.

2. The method according to claim 1, further comprising the step of reacting the compound of formula IV with MY to provide the compound of formula V:

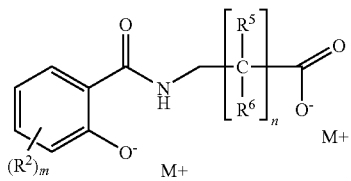
(V)

where M is an alkali metal and Y is a basic counter anion.

3. A method according to claim 2, wherein the metal M is Na.

4. A method according to claim 2, wherein Y is OH.

5. A method of claim 2, wherein the compound (V) is a hydrate.

6. A method according to claim 1 wherein MY is NaOH.

7. A method according to claim 1 wherein $NR^3R^4$ formula II is $NH_2$.

8. A method according to claim 1 wherein $R^2$ is Cl.

9. A method according to claim 1, wherein $R^2$ is located at position 5.

10. A method according to claim 1, wherein m is 1.

11. A method according to claim 1 wherein n is 6.

12. A method according to claim 1 wherein each $R^5$ and every $R^6$ is hydrogen.

13. A method according to claim 1 wherein the compound of formula IV is the compound (X):

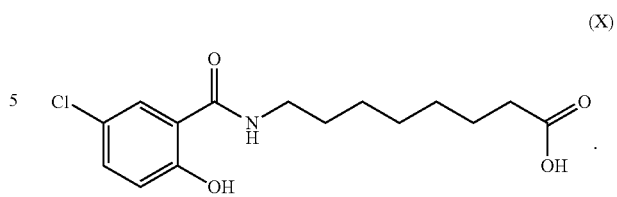
(X)

14. A method according to claim 2 wherein the compound of formula V is the compound (XI):

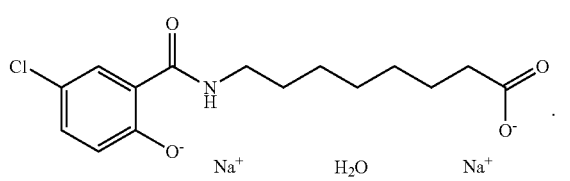
(XI)

15. The method of claim 1 further comprising making a compound of formula (IV), into pharmaceutical formulation, the pharmaceutical formulation additionally having at least one active ingredient.

* * * * *